United States Patent [19]

Nomori et al.

[11] 3,996,303
[45] Dec. 7, 1976

[54] ORGANIC HALIDE

[75] Inventors: Hiroyuki Nomori; Takuo Kawaguchi, both of Kurashiki; Kozo Nakao, Okayama; Masahisa Tanomura; Takashi Nishida, both of Kurashiki; Toshiaki Takagi; Kazuo Itoi, both of Kurashiki, all of Japan

[73] Assignee: Kuraray Co., Ltd., Kurashiki, Japan

[22] Filed: June 14, 1974

[21] Appl. No.: 479,413

Related U.S. Application Data

[62] Division of Ser. No. 194,565, Nov. 1, 1971, Pat. No. 3,862,212.

[52] U.S. Cl. .................. 260/654 R; 260/476 R; 260/488 H; 260/489; 260/491; 260/631 R
[51] Int. Cl.² ......................... C07C 21/00
[58] Field of Search .................. 260/654 R

[56] References Cited

UNITED STATES PATENTS 3,290,397  12/1966  Rust et al. .............. 260/654 R
3,370,098  2/1968  Illingworth ............. 260/654 R

OTHER PUBLICATIONS

Chem. Abstracts 47:1033h (1953).
J. of Org. Chem. of the U.S.S.R. 1, 2148–2156 corresponding to Zhurnal Organicheskoj Khemii 1, 2105–2114 (1965).

*Primary Examiner*—Delbert E. Gantz
*Assistant Examiner*—Joseph A. Boska
*Attorney, Agent, or Firm*—Bacon & Thomas

[57] ABSTRACT

An organic halide (1) having the general formula:

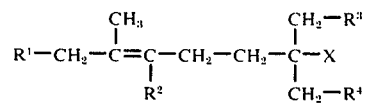

wherein X is a halogen atom, $R^1$, $R^2$, $R^3$ and $R^4$ is a hydrogen atom, a hydrocarbon group or a halogenated hydrocarbon group, $R^1$ may be a group having the formula:

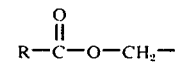

wherein R is an aliphatic, alicyclic or aromatic radical, and $R^3$ and $R^4$ may be a group consisting of -$CH_2OH$ or its esters; is produced by reacting an organic halide (2) having the formula:

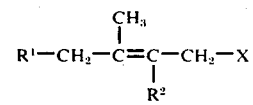

wherein X, $R^1$ and $R^2$ is the same as above, respectively; with the compound having the formula:

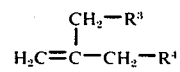

wherein $R^3$ and $R^4$ is the same as above, respectively, in the presence of a cationic catalyst at the temperature of from -78° C. to 80° C.

1 Claim, No Drawings

ORGANIC HALIDE

This is a division of application Ser. No. 194,565, filed Nov. 1, 1971, now U.S. Pat. No. 3,862,212.

This invention relates to a novel product which is industrially useful and a method of preparing the same, and more particularly to the organic halide having the following generic formula:

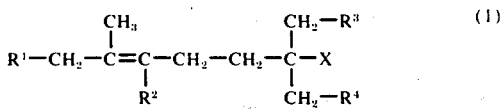

wherein X is a halogen atom, such as chlorine or bromine, $R^1$, $R^2$, $R^3$ and $R^4$ represent a hydrogen atom, a hydrocarbon group or a halogenated hydrocarbon group, $R^1$ may be a group having the formula:

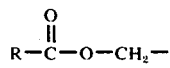

wherein R is an aliphatic, alicyclic or aromatic group, and $R^3$ and $R^4$ may be a group $-CH_2OH$ or its esters; which is abridged hereinafter as "organic halide (1)," and a method of producing the same.

The organic halide (1) provided according to the present invention are industrially useful, for example, as intermediates for preparation of perfume materials, medicinal materials and the like, especially intermediates for the synthesis of terpenes.

The inventors have now found that an organic halide (1) can be easily obtained with a low cost by reacting an organic halide having the following formula:

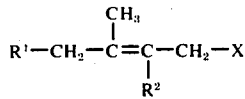

wherein X, $R^1$ and $R^2$ are the same as above, and $R^1$ may be a group having the formula

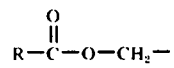

wherein R is an aliphatic, alicyclic or aromatic group; which is abridged hereinafter as "organic halide (2)," with the compound having the formula:

wherein $R^3$ and $R^4$ represent an hydrogen atom, a hydrocarbyl group, a halogenated hydrocarbon group or a group consisting of $-CH_2OH$ or its esters, which is abridged hereinafter as "olefin (3)" in the presence of a cationic catalyst, such as Lewis acids.

The reaction according to the present invention is a telomerization reaction in which the organic halide (2), such as 5-halo-3-methyl-3-pentenyl carboxylate serves as the telogen and olefin (3) such as isobutene as the taxogen. This reaction can be expressed by the following equation:

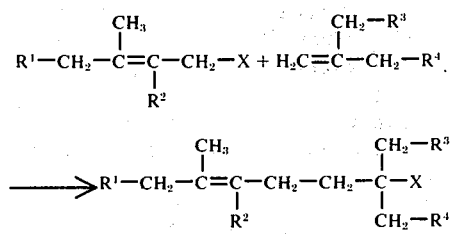

wherein X, $R^1$, $R^2$, $R^3$ and $R^4$ represent the same as above.

This reaction can be carried out in the presence of a cationic catalyst, such as Lewis acids, and in the presence or absence of a solvent under normal or increased pressure, by bringing the organic halide (2) into contact with the excess amount of the olefin (3).

In the description of Zhurnal Organicheskoj Khimii 1 2105 - 2114 (1965), it has been proposed that the molar ratio of olefin to organic halide should be regulated in the range of 1 : 1 or below 1 : 1 to obtain the additive products consisting of 1 mol of the telogen and 1 mol of the taxogen, and there 2,6-dimethyl-2-heptenyl-6-halide is obtained from 3-methyl-2-butenyl-1-halide as the organic halide and isobutene as the olefin by the telomerization reaction. But in this case, the yield of said additive product is only in the range of 12.5 to 14.0 per cent based on the weight of used 3-methyl-2-butenyl-1-halide in spite of the degree of the reaction i.e. the degree of the telomerization, is up to 80 to 86 per cent. And it is also known that the yield of the additive product from 1 mol of telogen and 1 mol of taxogen is decreased, and the poly additives such as dimers or trimers are increased, when the molar ratio of olefin to organic halides regulated in the range of more than 1.0; that is, heretofore the molar excess of olefin to that of organic halide has been used in the telomerization reaction system. Therefore, many prior arts have attempted to proceed the telomerization reaction under the condition of the molar excess of organic halide.

But, on the contrary of the mode of the known process, it is found that the yield of the additive product from 1 mol of the organic halide (2) as the telogen, and 1 mol of the olefin (3) as the taxogen is remarkably increased under the condition of reacting the telogen in the presence of the molar excess of the taxogen and regulating the temperature of said reaction in the range of about $-78°$ C to about $80°$ C., preferably $0°$ C. to $60°$ C.

The following processes may be applicable on the practice of the present invention. One of the processes comprises mixing the solution consisting of the organic halide (2) and the molar excess for the mol of the halide (2) of olefin (3) with the cationic catalyst and starting the telomerization reaction. Another process comprises mixing the organic halide (2) dropwise into the solution consisting of olefin (3) and the cationic catalyst and starting the telomerization reaction. On the practice of the present invention, the latter process is the most preferable since the organic halide (2) is more unstable in the reaction system and the desired product can be obtained more effectively by the latter process.

In the organic halide (1) represented by the general formula described above, 2,6-dimethyl-2-heptenyl-6- halide; which is the reaction product of 3-methyl-2-butenyl-1-halide and isobutene, wherein said $R^1$, $R^2$, $R^3$ and $R^4$ radicals in the above described general formula are hydrogen atoms; is the known product as described in Zhur. Org. Khim., 1 2105 – 2114 (1965), but other products are novel products which are not described in the prior art.

Representative examples of the organic halide (2) used as one of the starting materials in the present invention include a. Organic halides, whose said $R^1$ and $R^2$ is a hydrogen atom hydrocarbon groups, preferably, alkyl groups or alkenyl groups having the carbon numbers of from 1 to 6, halogenized hydrocarbon groups, preferably halogenated alkyl groups or halogenated alkenyl groups having the carbon numbers of from 1 to 6; such as 3-methyl-2-butenyl-1-halide, 3-methyl-2-pentenyl-1-halide, 3-methyl-2-hexyenyl-1-halide, 3-methyl-2-heptenyl-1-halide, 3,7-dimethyl-2-octenyl-1-halide, 3,7-dimethyl-2-nonenyl-1-halide, 2,3-dimethyl-2-butenyl-1-halide or 3-methyl-2-pentenyl-1,5-dihalide, and b. Organic halides whose said R is a ester group, such as 5-halo-3-methyl-3-pentenyl carboxylate having the following formula:

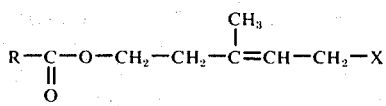

wherein R is an aliphatic, alicyclic or aromatic hydrocarbon radical, preferably an alkyl radical of 1 to 6 carbon atoms, phenyl radical or benzyl radical, and X is a halogen atom, preferably chlorine or bromine.

Representative examples of the compound represented by the formula (3), which may be used as the other starting material of the present invention, include 2-alkyl-1-alkene such as isobutene, 2-methyl-1-butene, 2-methyl-1-pentene, 2-methyl-1-hexene, 2-methyl-1-heptene, 2-ethyl-1-butene, 2-ethyl-1-pentene, 2-ethyl-1-hexene, 2-ethyl-1-heptene or 2-n-propyl-1-pentene; 2,6-dimethyl-1-heptene, 2,6-dimethyl-1,5-heptadiene, 2-ethyl-6-methyl-1-heptadiene. Other examples are the compounds whose $R^3$ or $R^4$ is —$CH_2OH$ group, such as isopropenyl ethyl alcohol, and the esters thereof. It is preferable to use the esters of isopropenyl alcohol instead of isopropenyl alcohol itself in the practice of the invention, since cationic catalyst are used in the present invention.

The "cationic catalyst" used in the invention means a material, such as Lewis acids, which can accelerate a cationic polymerization. Examples of the cationic catalysts are: (1) such metal halides as $AlCl_3$, $FeCl_3$, $SnCl_4$, $SbCl_5$, $TiCl_4$, $TeCl_2$, $TeCl_4$, $BiCl_3$ and $ZnCl_2$ which are commonly known as Friedel-Crafts catalysts, (2) complexes of the foregoing metal halides and electron donors, (3) boron halides and complexes of said boron halides and electron donors, (4) quarternary ammonium salts, (5) organic electron acceptors such as tetracyanoethylene, and (6) charge-transfer complexes of organic electron acceptors and electron donors. These catalysts can be used singly or in combination of at least two species. Particularly suitable cationic catalysts are aluminum chloride, ferric chloride, stannic chloride and zinc chloride. The amount of the catalyst to be used in the reaction may be varied within the range where the telomerization reaction can proceed without being inhibited by the impurities being present in the telomerization reaction system. It is generally effective on the reaction to use the catalyst in amounts of at least 0.001 mole, preferably 0.005 to 0.1 mole per mole of the organic halide (2).

In cases where the reaction is carried out in a solvent medium, the solvent should be a material which can neither deactivate the catalyst nor readily undergo a Friedel-Crafts reaction with the halide. For example, pyridine, thiophene and the like which have a high basicity can not be used as the solvent. On the other hand, by adding to the reaction system a suitable amount of ethyl alcohol, diethyl ether or the like whose basicity is not so strong it is possible to lower the activity of the catalyst and control the progress of the reaction. The materials which can be generally used as the solvent in the reaction are, for example, acyclic ethers such as diethyl ether and diisopropyl ether, cyclic ethers such as dioxane and tetrahydrofuran, halogenated hydrocarbons such as 1,2-dichloroethane and dichloromethane, and such aromatic compounds as benzene which is relatively free from a Friedel-Crafts reaction.

The temperature for the telomerization reaction may be lower than the ceiling temperature for polymerization of isobutene. The preferred reaction temperature ranges from −78° C. to 80° C. especially from 0° C. to 60° C. This reaction is considerably exothermic, and therefore it is necessary to cool the reaction system itself and/or carrying out the reaction in a reactor equipped with a reflux condenser or an autoclave in which the reaction system can be sealed, so as to prevent the volatilization of the reaction system. In a preferable embodiment of the invention, the reaction is carried out using an ether having a low boiling point as the solvent and a reactor equipped with a reflux condenser, whereby excessive elevation of the temperature of the reaction system and consequent increase of side reactions as well as the volatilization of the reaction system can be easily prevented.

In the telomerization reaction according to the invention, the cation from the organic halide (2), for example 5-acyloxy-3-methyl-2-pentenyl cation which should be present in the process of the reaction localizes its positive charge on the carbon of 1-position, the said cation is moderately stabilized by allyl resonance, the olefine (3), for example isobutene is particularly electronegative on the carbon of 1-position through hyperconjugation effect of its methyl group, and these facts in concert with steric factor contribute to make the reaction proceed on the 1-position of the cation from the organic halide (2), for example, 5-acyloxy-3-methyl-2-pentenyl cation and the 1-position of the olefin (3) for example, isobutene preferentially. Accordingly, the direction, position and mode of the reaction are restricted and thus the desired product, for example 7-halo-3,7-dimethyl-3-octenyl carboxylate can easily be isolated from the reaction system by an ordinary method such as distillation.

The organic halide (1) for example 7-halo-3,7-dimethyl-3-octenyl carboxylates provided according to the present invention are industrially useful, for example, as intermediates for preparation of perfume materials, medicinal materials and the like. For instance, citronella oil by complicated treatments can be easily synthesized from the 7-halo-3,7-dimethyl-3-octenyl carboxylates through hydrogenation, dehydrohalogenation and solvolysis (hydrolysis or alcoholysis) in this order. Further, the 7-halo-3,7-dimethyl-3-octenyl carboxylates can be transformed to mono-terpene alcohols consisting of 3,7-dimethyl-3,6-octadiene-1-ol and 3,7-dimethyl-3,7-octadiene-1-ol through dehydrohalogenation and subsequent solvolysis (hydrolysis or alcoholysis). Furthermore, hydroxycitronellol can be obtained by hydrolysis of 7-halo-3,7-dimethyl-octyl carboxylates which is prepared by hydrogenating the 7-halo-3,7-dimethyl-3-octenyl carboxylates.

The 5-halo-3-methyl-3-pentenyl carboxylate which is used as one of the starting materials in the method according to the present invention may be represented by the general formula:

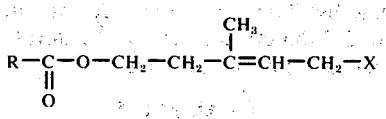

wherein R is an aliphatic, alicyclic or aromatic hydrocarbon radical, preferably an alkyl radical of 1 to 6 carbon atoms, phenyl radical or benzyl radical, and X is a halogen atom, preferably chlorine or bromine. In view of the cost, easiness of production and handling, the most preferred 5-halo-3-methyl-3-pentenyl carboxylate is 5-chloro-3-methyl-3-pentenyl acetate. The 5-halo-3-methyl-3-pentenyl carboxylates have not heretofore been known in the art, but can be easily prepared at a high yield by reacting 4-methyl-5,6-dihydro—(2H)-pyran and an acyl halide represented by the general formula

wherein R and X are the same as the foregoing, in the presence of a cationic catalyst according to a method disclosed in our copending patent application. 4-methyl-5,6-dihydro-(2H)-pyran is a well known compound, abundantly by-produced in the manufacture of isoprene from isobutene and formaldehyde.

AN EXAMPLE OF SYNTHESIS OF 5-HALO-3-METHYL-3-PENTENYL CARBOXYLATE 245 grams of 4-methyl-5,6-dihydro-(2H)-pyran was dissolved into 500 milliliters of benzene in a reactor, in which 12.5 grams of zinc chloride was suspended, and into the suspension was added dropwise 196 grams of acetyl chloride in 6 hours 55 minutes. During the foregoing operation the reactor was cooled in an ice-water bath to maintain the reaction temperature below 5.5° C. After the completion of the dropwise addition of acetyl chloride the system was still cooled in the ice-water bath for 35 minutes while stirring. Then, 100 milliliters of water was added to the reaction system, still continuing cooling the system with ice-water, whereby the reaction was stopped. The temperature rise of the reaction system at the time of adding water was only up to 25.5° C. The aqueous layer was then separated from the benzene layer of the reaction system, and the benzene layer was washed with 100 milliliters of water three times and subsequently with 100 milliliters of saturated aqueous solution of sodium bicarbonate twice. Then, under slightly reduced pressure benzene was distilled off from the benzene layer, and by subsequent distillation a fraction of the boiling point range of lower than 87.0° C./3.1mmHg was collected to obtain 264.7 grams of 5-chloro-3-methyl-3-pentenyl acetate. The product obtained as above was identified to be a mixture of both cis- and trans-isomers on their y - g double bond by nuclear magnetic resonance spectroscopy. The product is a colorless transparent liquid having a sweet apple-like odor, boiling in the range of 82.8° C./3.0mmHg - 85.2° C./2.8mmHg, showing elementary analytic values; C, 54.7%; H, 7.5%; Cl, 19.8%; O, 18.0%; refractive index, $n_D^{30}$; 1.4606; and density, $p_4^{30}$; 1.0623.

The present invention will be described in more detail by the following examples which are intended only to illustrate the invention.

EXAMPLE 1

13g of 2,6-dimethyl-1,5-heptadiene (geraniolene) and 30ml of ethyl ether were placed into a three necked flask having the capacity of 100ml, and were cooled below −10° C. 10cc of stannic tetrachloride was added into the above reagents. Then the temperature of these reagents were gradually raised up to 0° C. by iced water with stirring. 20g of 5-chloro-3-methyl-3-pentenyl acetate was added dropwise into the above reagents during 40 minutes. During the dropwise addition of 5-chloro-3-methyl-3-pentenyl acetate, the temperature of the reaction system reached at 5° C. The reaction was continued for 60 minutes under the condition of the temperature of 0° C. with stirring. After the completion of reaction, the reaction mixture was separated into the aqueous layer and the organic layer, and the organic layer was washed with water for several times to remove the catalyst. Then, the organic layer was dried with calcium chloride. The yield of the desired product, which was the reaction product of 1 mol of 2,6-dimethyl-1,3-heptadiene and 1 mol of 5-chloro-3-methyl-3-pentenyl acetate and had the following structure;

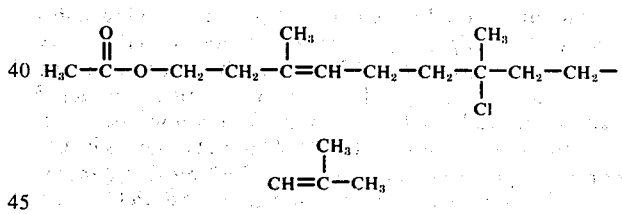

in the organic layer, was measured by gas chromatographic analysis using methyl heptenone as the internal standard. The yield reached 50.9 per cent based on the weight of 5-chloro-3-methyl-3-pentenyl acetate used in the reaction, and 2 per cent of the unreacted 5-chloro-3-methyl-3-pentenyl acetate was remained in the product.

Control example

The same reagents and the same content of the reagents used in Example 1 were reacted under the following conditions 2,6-dimethyl-1,5-pentadiene was placed into the flask and was cooled below −10° C, and then, ethyl ether, 5-chloro-3-methyl-3-pentenyl acetate and stannic tetrachloride was added into said flask. The temperature of the reagents was gradually raised up to 0° C with stirring, and the reaction was continued for 100 minutes. During the reaction, the temperature reached at 95° C. After the completion of the reaction, the yield of the purpose product was measured by the same process described in Example 1. But the yield was only 19.2 per cent based on the weight of 5-chloro-3-methyl-3-pentenyl acetate. And 5-chloro-3-methyl-3-pentenyl acetate was not retained in the product.

EXAMPLE 2

500ml of liquid isobutene was placed in the glass autoclave having the capacity of 1, which was previously cooled by the coolant consisting of dry ice and acetone at −78° C. Then, 10ml of stannic tetrachloride and 300g of 5-chloro-3-methyl-3-pentenyl acetate were added into the autoclave under the same temperature described above. After the autoclave was sealed, the temperature of the autoclave was gradually raised up to 0° C. by iced water and the stirring was continued for 120 minutes to react the reagents. During the stirring the temperature of the reaction system reached up to 60° C. and the inner pressure of the autoclave reached at 5 kg/cm². After the completion of the reaction, the reaction mixture was separated into the aqueous layer and the organic layer, and the organic layer was washed with water for several times. The organic layer was dried by the same process described in Example 1.

The yield of the desired product, which was the reaction product of 1 mol of isobutene and 1 mol of 5-chloro-3-methyl-3-pentenylacetate and had the following structure:

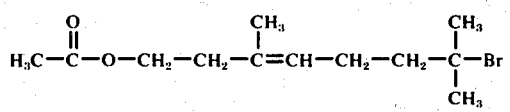

in the organic layer, was measured by the same process described in Example 1. The yield of the above described product was 69.5 per cent based on the weight of 5-chloro-3-methyl-3-pentenyl acetate used in the reaction and 5-chloro-3-methyl-3-pentenyl acetate didn't remained in the product.

EXAMPLE 3

500ml of liquid isobutene was placed in a glass autoclave of 1 capacity, which had been cooled by dry ice-acetone coolant at −78° C. Then, 10ml of stannic chloride and 376g of 5-bromo-3-methyl-3-pentenyl acetate were added. Operating the reaction and treating the reaction product in the same manner as in Example 2, the desired product, i.e. 7-bromo-3,7-dimethyl-3-octenyl acetate, was obtained in the yield of 58 percent based on the fed 5-bromo-3-methyl-3-pentenyl acetate.

EXAMPLE 4

500ml of liquid isobutene was placed into the glass autoclave having the capacity of 1, which was previously cooled by the coolant consisting of dry ice and acetone at −78° C. Then, 12g of zinc chloride and 100g of 3,7-dimethyl-2-octenyl-1-chloride were added into the autoclave under the same temperature described above. After the autoclave was sealed, the temperature of the autoclave was raised gradually up to 0° C. by iced water and the stirring was continued for 90 minutes to react the reagents. During the reaction, the temperature of the reaction mixture reached up to 45° C. and the inner pressure of the autoclave reached at 4.0 kg/cm². After the inner pressure was reduced to the atmospheric pressure, 200cc of iced water was added into the autoclave to stop the reaction, and the reaction mixture was separated into the aqueous layer and the organic layer. The organic layer was washed with water for several times to remove the catalyst, i.e. zinc chloride, and then dried with calcium chloride.

The yield of the desired product, which was the reaction product of 1 mol of isobutene and 1 mol of 3,7-dimethyl-2-octenyl-1-chloride and had the following structure;

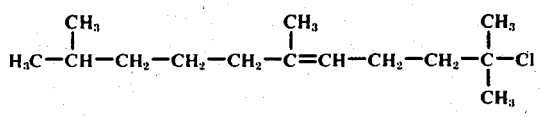

in the organic layer, was measured by the same process described in Example 1. The yield of the above described product was 72.3 per cent based on the weight of 3,7-dimethyl-2-octenyl-1-chloride used in the reaction, and 3,7-dimethyl-2-octenyl-1-chloride was not entirely remained in the product.

EXAMPLE 5

150ml of isobutene was placed into the glass autoclave having the capacity of 1, which was previously cooled by the coolant consisting of dry ice and acetone at −78° C. Then, 200ml of ethyl ether and 12g of zinc chloride were added into the autoclave and the temperature of said reagents was raised up to 0° C. by iced water with stirring. On the other hand, 150g of 3-methyl-1,5-dichloro-3-pentene (3-methyl-2-pentenyl-1,5-dichloride) was placed into an other pressure bottle and said bottle was connected with the autoclave with sealect system. Said 3-methyl-1,5-dichloro-3-pentene was added dropwise into the autoclave in 60 minutes. During the dropwise addition, the temperature of the reaction mixture was raised up to 10° C. After the completion of the dropwise addition, the reaction mixture was stirred for 60 minutes under the cooling condition by iced water. The reaction mixture was processed by the same process described in Example 2, and the same analysis described in said Example was processed. The yield of the desired product, which was the reaction product having the following structure:

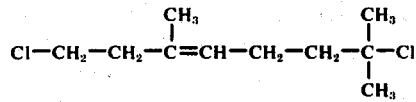

was 56.5 per cent based on the weight of 3-methyl-1,5-dichloro-3-pentene used in the reaction and 1,5 per cent of the unreacted 3-methyl-1,5-dichloro-3-pentene was remained in the product.

EXAMPLE 6

500ml of isobutene was placed into the glass autoclave having the capacity of 1, which was previously cooled by the coolant consisting of dry ice and acetone. Then, 10ml of stannic tetrachloride and 150g of 2,3-dimethyl-2-butenyl-1-chloride were added into the autoclave under the same temperature. After the autoclave was sealed, the temperature was gradually raised up to 0° C. with iced water and the stirring was continued for 120 minutes to proceed the reaction. After the reaction was stopped by adding iced water, the reaction mixture was separated into aqueous layer and the organic layer. The organic layer was washed with water for several times to remove the catalyst, i.e. stannic tetrachloride, and was processed by the same process described in Example 1.

The yield of the desired product, which was the reaction product of 1 mol of isobutene and 1 mol of 2,3-dimethyl-2-butenyl-1-chloride and had the following structure:

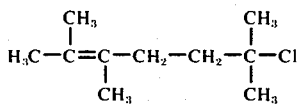

in the organic layer, was 65.2 per cent based on the weight of 2,3-dimethyl-2-butenyl-1-chloride used in the reaction. And none of 2,3-dimethyl-2-butenyl-1-chloride was in the product.

EXAMPLE 7

500ml of liquid isobutene was placed into the glass autoclave having the capacity of 1, which had been cooled by the coolant consisting of dry ice and acetone. Then 12g of zinc chloride and 150ml of 3-methyl-2-butenyl-1-chloride (purity: 92.5 weight per cent) were added into the autoclave under the same temperature. After the autoclave was sealed, the temperature was gradually raised up to 0° C. with iced water and the stirring was continued for 90 minutes to proceed the reaction. During the reaction, the temperature of the reaction system was raised up to 50° C., and the inner pressure reached up to 4.5 kg/cm². After the pressure was reduced to the atmospheric pressure, the reaction was stopped by adding 200ml of iced water into the reaction mixture, and the reaction mixture was separated into aqueous layer and the organic layer. The organic layer was washed with water for several times to remove zinc chloride, and dried with calcium chloride. The yield of the desired 2,6-dimethyl-2-heptenyl-6-chloride, which was the reaction product of 1 mol of isobutylene and 1 mol of 3-methyl-2-butenyl-1-chloride and had the following structure:

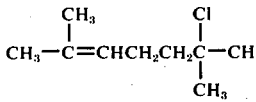

in the organic layer, was measured by gas chromatographic analysis using methyl heptenone as the internal standard. The yield of said product was 75.7 per cent based on the weight of 3-methyl-2-butenyl-1-chloride used in the reaction, and 2 per cent of the unreacted 3-methyl-2-butenyl-1-chloride was still remained in the product.

EXAMPLE 8

113ml of liquid isobutene was placed into the glass autoclave having the capacity of 1, which had been cooled by the coolant consisting of dry ice and acetone. Then, 200ml of methylene chloride, 5ml of ethanol and 10ml of stannic tetrachloride were added into the autoclave under the same temperature. During the temperature was gradually raised by iced water, 150ml of 3-methyl-2-butenyl-1-chloride (purity 92.5 per cent) was added dropwise into the autoclave during 120 minutes to react said reagents. After the completion of the dropwise addition, the reaction mixture was stirred for 60 minutes under the temperature of 0° C. During the reaction, the temperature of the reaction system was raised up to about 4° C., and the inner pressure of the autoclave was raised up to 1.9 kg/cm². After the pressure was reduced to the atmospheric pressure, 200cc of iced water was added into the reaction mixture to stop the reaction. The reaction mixture was separated into the aqueous layer and the organic layer. The organic layer was washed with water for several times to remove stannic tetrachloride, and then was dried with calcium chloride.

The yield of the desired product, 2,6-dimethyl-2-heptenyl-6-chloride, which was the reaction product of 1 mol of isobutene and 1 mol of 3-methyl-2-butenyl-1-chloride, in the product, was 51.9 per cent based on the weight of 3-methyl-2-butenyl-1-chloride used in the reaction. And 3-methyl-2-butenyl-1-chloride was scarcely remained in the product.

The present example was processed by the same ratio between the organic chloride and the olefin according to the method described in the Zhur. Org. Khim., 1 2105–2114 (1965) which was described formerly. But the yield of the present product was remarkably high than that of the above mentioned description, which is in the range of 12.5 to 14.0 per cent.

On the other hand, for the comparison, the same reagents and the same content of the reagents used in the present example were reacted under the following conditions. Isobutene was placed into the autoclave under the condition of the temperature cooled by dry ice, and then, methylene chloride, 3-methyl-2-butenyl-1-chloride and stannic tetrachloride were placed into said autoclave. The reaction system was raised up to 0° C. with stirring for 180 minutes. The temperature in the autoclave was raised up to 90° C. After the reaction was stopped, the reaction mixture was treated with the same process described in the present example. But the yield of 2,6-dimethyl-2-heptenyl-6-chloride was at most 19.2 per cent based on the weight of 3-methyl-2-butenyl-1-chloride used in the reaction, and none of 3-methyl-2-butenyl-1-chloride was in the product.

EXAMPLE 9

45g of 2,6-dimethyl-1,5-heptadiene, 20ml of diethyl ether, 0.5ml of ethanol and 100ml of stannic tetrachloride were placed into the flask having the capacity of 200ml and equipped with the stirrer. Then, 14g of 3-methyl-2-butenyl-1-chloride, which was the same reagent used in Example 7, was added dropwise during 40 minutes with stirring and under the temperature of 0° C. The reaction was continued for 60 minutes under the same condition. After the completion of the reaction, the reaction mixture was separated into aqueous layer and the organic layer. The organic layer was washed with water for several times to remove the catalyst and the product was analysed by the same process described in Example 7. From the result of the analysis, it was known that 3-methyl-2-butenyl-1-chloride used in the reaction was entirely converted, and the yield of the desired product, 2,6,10-trimethyl-6-chloro-2,9-undecadiene was 68 per cent based on the weight of 3-methyl-2-butenyl-1-chloride used in the reaction.

EXAMPLE 10

52g of 2,6-dimethyl-6-hepten-3-one, 30g of ethyl ether (solvent) and 3ml of benzene solution of 33 weight per cent of stannic tetrachloride were placed into a three necked flask having the capacity of 200cc and having the stirrer under the temperature of 0° C. Then, 13g of 3-methyl-2-butenyl-1-chloride was added dropwise during 30 minutes from the dropfunnel under the temperature of 0° C. The added reagents were stirred for 60 minutes at 0° C. to react them. After the reaction was stopped, the product was washed with water for several times to remove the catalyst and was analysed by the gas chromatography.

The yield of the desired product, 6-chloro-2,6,10-trimethyl-9-undecen-2-one, which was the reaction product of 1 mol of 2,6-dimethyl-6-hepten-3-one and 1 mol of 3-methyl-2-butenyl-1-chloride was 46.0 per cent based on the weight of 3-methyl-2-butenyl-1-chloride used in the reaction.

EXAMPLE 11

100ml of 5-chloro-3-methyl-3-pentenyl acetate was dissolved into 200ml of diethyl ether (dried over sodium wire), and while the resultant solution was cooled with ice-water, 50.2ml of isobutene at 0° C. was dissolved therein. To the above solution which was placed in a reactor equipped with a dry-ice acetone reflux condenser, 10ml of anhydrous stannic chloride was added dropwise in 8 minutes 25 seconds. After two hours' reaction with cooling and stirring, 100ml of water was added to the reaction system to stop the reaction. Then, the reaction mixture was separated into the aqueous layer and the organic layer, and the organic layer was washed with 100 ml of water once and subsequently with 100ml of saturated aqueous solution of sodium bicarbonate twice. By aspiration with an aspirator at room temperature the ether was distilled off from the organic layer, whereby 109.7 grams of a viscous yellowish liquid was obtained. A gas-chromatographic analysis of the viscous liquid revealed that the liquid contained 19.7 grams of 7-chloro-3,7-dimethyl-3-octenyl acetate. The 7-chloro-3,7-dimethyl-3-octenyl acetate isolated by distillation had a boiling point of 92.0° – 97.2° C./3.4mmHg, refractive index $n_D^{30}$; 1.4570; density $p_4^{30}$; 0.9351; specific refraction $r_D$; 0.2912.

EXAMPLE 12

7.0 grams of ferric chloride was dissolved in 100 milliliters of diethyl ether dried over sodium wire, and in the solution was further dissolved 25ml of isobutene at 0° C. while cooling the system in an ice-water bath. To the above ether solution which was placed in a reactor equipped with a dry-ice-acetone reflux condenser, 50ml of 5-chloro-3-methyl-3-pentenyl acetate was added dropwise in as short a time as possible. After a short induction period highly exothermic reaction commenced, and the reaction system came to a boil. After two hours' reaction with cooling and stirring, 50ml of water was added to the reaction system, whereby the reaction was stopped. The reaction mixture was separated into the aqueous layer and the organic layer, and the organic layer was washed with 50ml of saturated aqueous solution of sodium bicarbonate twice and then with 50ml of water once. By aspiration at room temperature the ether was distilled off from the organic layer, whereby 50.8 grams of a viscous liquid was obtained. It was found by gas-chromatographic analysis of the liquid that 4.68 grams of 7-chloro-3,7-dimethyl-3-octenyl acetate had been formed in the above reaction.

EXAMPLE 13

50ml of isobutene at 0° C. was added to a mixture of 10 grams of zinc chloride, 100ml of 5-chloro-3-methyl-3-pentenyl acetate and 200ml of benzene which had been placed in a reactor equipped with a dry-ice-acetone reflux condenser and cooled in an ice-water bath. The reaction was continued with stirring and cooling. After 2 hours' reaction 100ml of water was added to the reaction system, whereby the reaction was stopped. The reaction mixture was then treated in the same manner as in Example 11, whereby it was found that 15 grams of 7-chloro-3,7-dimethyl-3-octenyl acetate had been formed in the above reaction.

EXAMPLE 14

In a flask equipped with a dry-ice-acetone reflux condenser were placed 23.9 grams of 5-chloro-3-methyl-3-pentenyl benzoate, 5.6 grams of isobutene and 100ml of 1,2-dichloroethane. To the mixture in the flask was added dropwise a catalyst solution consisting of 1 ml of tin tetrachloride (=stannic chloride) and 0.5ml of ethanol while stirring and cooling the system in an ice-water bath. The system was reacted for two hours with cooling and stirring, and then the reaction was stopped by adding 100ml of water to the system. The reaction mixture was further treated in the same manner as in Example 11, whereby 14.5 grams of 7-chloro-3,7-dimethyl-3-octenyl benzoate was obtained.

EXAMPLE 15

The experimental procedures in Example 10 were repeated except that 10 grams of aluminium chloride was used as the catalyst instead of zinc chloride. As the result, 12 grams of 7-chloro-3,7-dimethyl-3-octenyl acetate was obtained.

EXAMPLE 16

20g of isopropenylethyl acetate and 30cc of ethyl ether were placed into a three necked flask having the capacity of 100ml, and were cooled below −10° C. to make a ethyl ether solution of isopropenyl ethyl acetate. 10ml of stannic tetrachloride was added into the solution above. Then the temperature of the solution was gradually raised up to 0° C. by iced water. 10g of 3-methyl-2-butenyl-1-chloride was added dropwise into the solution in 30 minutes with stirring. During the dropwise addition of 3-methyl-2-butenyl-1-chloride, the temperature of the reaction system reached at 10° C. The reaction was continued for 60 minutes at 0° C. After the completion of the reaction, the reaction mixture was separated into the aqueous layer and the organic layer, and the organic layer was washed with water for several times to remove the catalyst. Then, the organic layer was dried with calcium chloride. The yield of the desired product, 1,5-dimethyl-1-hydroxyethyl-4-hexenyl-1-chloride, and having the formula of

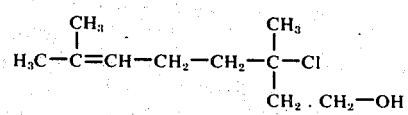

reached at 59.5 per cent based on the weight of 3-methyl-2-butenyl-1-chloride used in the reaction. And 3-methyl-2-butenyl-1-chloride was not retained in the product.

EXAMPLE 17

20g of isopropenyl ethyl acetate and 30cc of ethyl ether were placed into a three necked flask having the capacity of 100cc, and were cooled below −10° C. to make a ethyl ether solution of isopropenyl ethyl acetate. 1g of zinc chloride was added into the solution above. Then, the temperature of the solution was gradually raised up to 0° C by iced water. 15g of 1-chloro-3-methyl-2-pentenyl acetate was added dropwise into the solution 25 minutes. The reaction was continued for 60 minutes at 0° C. with stirring. After the same process described in Example 16 was processed to the product, the yield of the desired product, 7-chloro-3,7-dimethyl-7-hydroxy ethyl-3-heptenyl acetate, and having the formula of

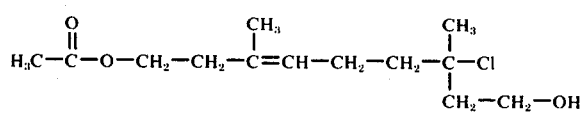

in the product was measured by the same process described in Example 1. The yield was reached at 60 per cent based on the weight of 1-chloro-3-methyl-2-pentenyl acetate used in the reaction. And said acetate was not retained in the product.

AN EXAMPLE OF SYNTHESIS OF CITRONELLOL 1 mole of 7-chloro-3,7-dimethyl-3-octenyl acetate was dissolved into 200 milliliters of dioxane and the solution was subjected to hydrogenation reaction in a reactor containing 20 grams of activated palladium black at about 25° C. under normal pressure until hydrogen was no more absorbed. Then, palladium black was filtered off, from the reaction mixture and dioxane was distilled off from the filtrate under reduced pressure. The residual liquid was added to the solution of 40 grams of sodium hydroxide in 200 milliliters of methanol, and heated under reflux for 72 hours. The resulting reaction mixture was diluted with 1200 milliliters of water, and the oil layer was separated from the aqueous layer. The oil layer thus separated was washed with 200 milliliters of water three times and then dried over 20 grams of Glauber's salt (sodium sulfate). By distillation of the oil layer under reduced pressure a fraction having a boiling point range of 110°–118° C./15mmHg was collected, whereby 0.7 mole of citronellol was obtained.

AN EXAMPLE OF SYNTHESIS OF HYDROXYCITRONELLOL 1 mole of 7-chloro-3,7-dimethyl-3-octenyl acetate was dissolved into 200 milliliters of dioxane and the solution was subjected to hydrogenation reaction in a reactor containing 20 grams of activated palladium black at about 25° C. under normal pressure until hydrogen was no more absorbed. Then, the palladium black was filtered off from the reaction mixture, and dioxane was distilled off from the filtrate. To the resulting residue were added 50 milliliters of water, 200 milliliters of acetone and 10 grams of silver oxide, and the mixture was heated under reflux for 72 hours. After filtrating off precipitate contained in the reaction mixture, acetone and water were distilled off from the filtrate. By distillation of the residual liquid a fraction boiling in the temperature range of 135°–145° C./4.0mmHg was collected, whereby 0.6 mole of hydroxycitronellol was obtained.

AN EXAMPLE OF SYNTHESIS OF 3,7-DIMETHYL-3,6-OCTADIENE-1-OL AND 3,7-DIMETHYL-3,7-OCTADIENE-1-OL 8.0 grams of 7-chloro-3,7-dimethyl-3-octenyl acetate, 3.96 grams of sodium hydroxide, 8 milliliters of ethanol and 0.203 milliliter of water were mixed and heated under reflux for one hour, and then 5 milliliters of water was added to the reaction system. The reaction system was further heated under reflux for 1 hour, and to the system was added again 20 milliliters of water to separate the oil layer from the system. The oil layer was washed with 10 milliliters of saturated aqueous solution of sodium bicarbonate twice. Then, the oil layer was distilled and a fraction boiling in the range of 80.0° – 83.0° C./2.5mmHg was collected, from which was obtained 4.0 grams of a mixture of 3,7-dimethyl-3,6-octadiene-1-ol and 3,7-dimethyl-3,7-octadiene-1-ol, the mixture being a colorless and transparent liquid of $n_D^{29.6} = 1.4717$.

What we claim:

1. An organic halide having the formula:

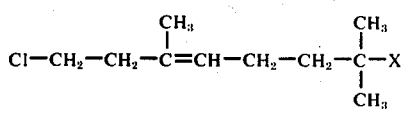

wherein X is a halogen atom.